United States Patent
Klee et al.

[11] Patent Number: 5,827,946
[45] Date of Patent: Oct. 27, 1998

[54] METHOD FOR SAMPLE IDENTIFICATION USING A LOCKED RETENTION TIME DATABASE

[75] Inventors: Matthew S. Klee, Wilmington, Del.; Philip L. Wylie, Kennett Sq.; Bruce D. Quimby, Lincoln University, both of Pa.; Leonid M. Blumberg, Hockessin, Del.

[73] Assignee: Hewlett-Packard Company, Palo Alto, Calif.

[21] Appl. No.: 846,977

[22] Filed: Apr. 30, 1997

[51] Int. Cl.⁶ .......................... G01N 30/02; G01N 21/01; B01D 15/08
[52] U.S. Cl. ................. 73/23.36; 73/23.27; 73/23.24; 422/89; 55/67; 210/198.2; 210/656
[58] Field of Search ................ 73/23.36, 23.39, 73/23.24, 23.23, 23.22, 61.57, 23.35; 55/67; 210/198.2, 656; 422/70, 89

[56] References Cited

U.S. PATENT DOCUMENTS

| | | | |
|---|---|---|---|
| 3,717,028 | 2/1973 | Annino et al. | 73/23.1 |
| 3,898,837 | 8/1975 | Boege | 73/23.1 |
| 4,181,613 | 1/1980 | Welsh et al. | 210/179 |
| 4,353,242 | 10/1982 | Harris et al. | 73/23.1 |
| 4,740,903 | 4/1988 | Nakatsuka et al. | 364/497 |
| 4,807,148 | 2/1989 | Lacey | 364/498 |
| 4,824,446 | 4/1989 | Mowery, Jr. | 55/67 |
| 4,927,532 | 5/1990 | Pospisil et al. | 210/198.2 |
| 4,994,096 | 2/1991 | Klein et al. | 55/20 |
| 5,106,756 | 4/1992 | Zaromb | 436/161 |
| 5,108,468 | 4/1992 | Ligon, Jr. | 55/67 |
| 5,116,764 | 5/1992 | Annino et al. | 436/161 |
| 5,163,979 | 11/1992 | Patrick et al. | 55/21 |
| 5,281,397 | 1/1994 | Ligon et al. | 422/89 |
| 5,339,673 | 8/1994 | Nakagawa et al. | 73/23.36 |
| 5,354,474 | 10/1994 | La Pack et al. | 210/637 |
| 5,398,539 | 3/1995 | Gordon et al. | 73/23.35 |
| 5,405,432 | 4/1995 | Snyder et al. | 95/82 |
| 5,436,166 | 7/1995 | Ito et al. | 436/161 |
| 5,492,555 | 2/1996 | Strunk et al. | 95/86 |
| 5,559,728 | 9/1996 | Kowalski et al. | 364/571.02 |
| 5,670,379 | 9/1997 | Ito et al. | 436/161 |

OTHER PUBLICATIONS

Hewlett–Packard Instruction Manual, Gas Chromatograph–Atomic Emission Detector Quick Screen Methods, GC–AED pp. 7–26, Sep. 20, 1994.

"Standard Test Method for Detailed Analysis Of Petroleum Naphthas Through n–Nonane By Capillary Gas Chromatography"; ASTM Committee D–2 on Petroleum Products and Lubircants; Published Oct. 1992, Originally published as D 5134–90.

Hewlett–Packard Company Operation Manual,"5880A Gas Chromatograph PNA Analyzer, Operation 850", Oct. 1983; Revised Jul. 1983; Part No. 18900–90850.

Hewlett–Packard Company Operation Manual, "The HP5880A Gas Chromatograph and The HP85 Computer Configured for PNA Analysis"; 18900–90603; Mar. 1985 Rev. B, Apr. 1986 Rev C.

*Primary Examiner*—Hezron E. Williams
*Assistant Examiner*—J. David Wiggins
*Attorney, Agent, or Firm*—Richard F. Schuette

[57] ABSTRACT

The invention provides a method for developing a retention time database of identified analytes and their respective retention times in a reference Gas Chromatograph (GC) system under locked conditions for identification of unknown analytes of interest eluting from any GC system locked to the retention time database and may also be employed in combination with selective detection and or method translation for enhanced certainty of identification.

8 Claims, 10 Drawing Sheets

RETENTION TIME ADJUSTMENT
USING RT VERSUS P CALIBRATIONS $$\text{PRESSURE ADJUSTMENT} = \frac{(RT_n - RT_{TARGET})}{\frac{\Delta RT}{\Delta P}}$$

FIG.3

RETENTION TIME LOCKING SOFTWARE
CALCULATES FINE ADJUSTMENT OF INLET
PRESSURE

RETENTION TIME LOCKING

CALIBRATION DATA

RTL CALIBRATION FILE NAME:
C:\HPCHEM\1\METHODS\CKO_RUN1.M\RT_LOCK
CALIBRATION DATE    MON FEB 24 22:04:35 1997

|  | PRESSURE | RET TIME |
|---|---|---|
| RUN 1 | 11 | 27.167 |
| RUN 2 | 13 | 25.692 |
| RUN 3 | 15 | 24.561 |
| RUN 4 | 17 | 23.644 |
| RUN 5 | 19 | 22.88 |
| PRESSURE UNITS |  | psig |
| CORR. COEF. |  | 0.99989 |
| TARGET RET TIME |  | 24.3 |
| TARGET COMPOUND |  | ENDRIN |

ENTER RET TIME OF TARGET PEAK       25.437

ENTER CURRENT INLET PRESSURE        15.4

SUGGESTED PRESSURE TO LOCK RT       17.569693

[CALC]   [DONE]

FIG.4

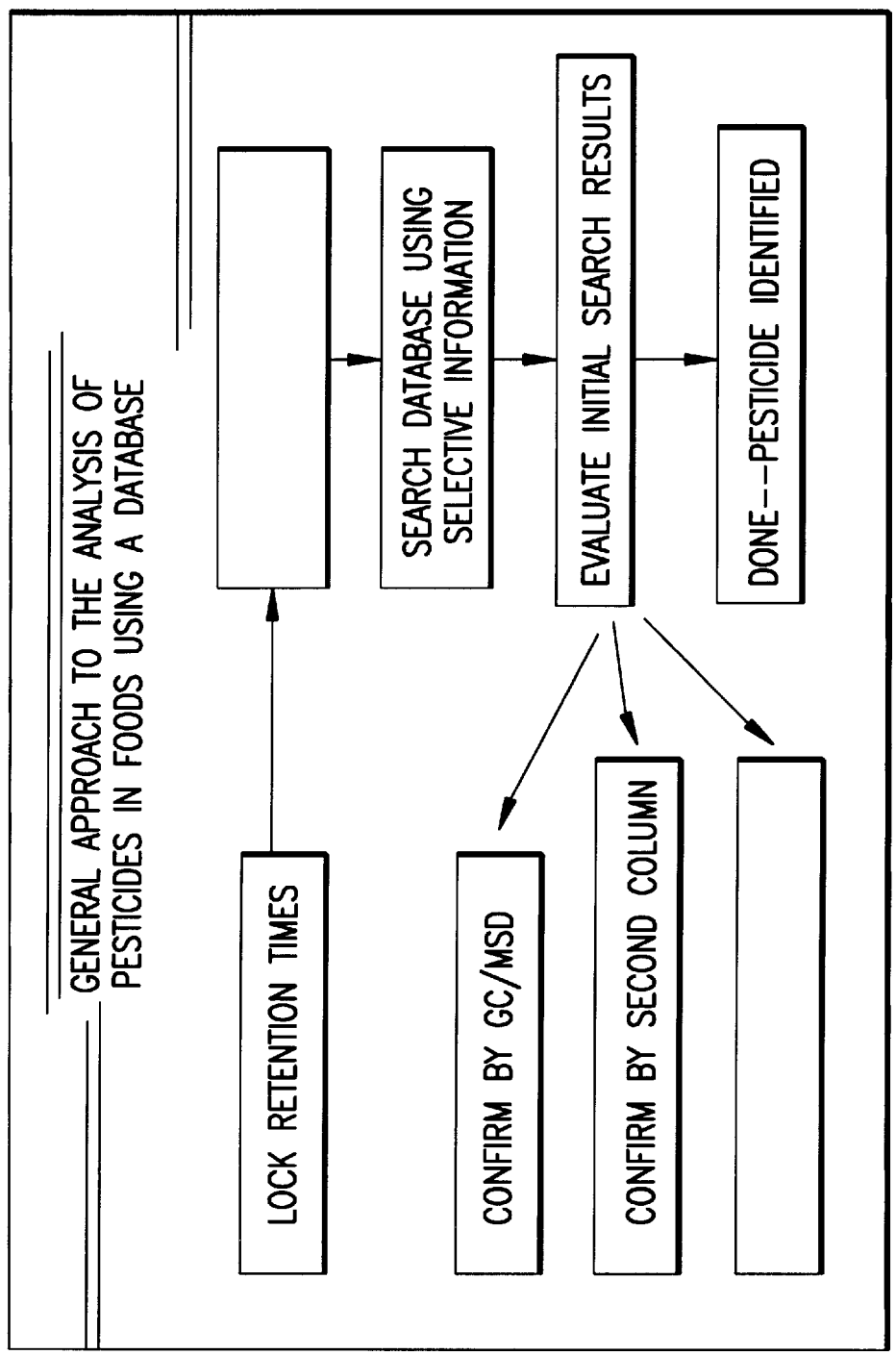

PESTICIDE SEARCH RESULTS

SEARCH RESULTS WITHOUT USING ELEMENT
DATA: 20 PESTICIDES IN TIME WINDOW

| START NEW REPORT | ADD RESULTS TO CURRENT REPORT |
| --- | --- |
| VIEW CURRENT REPORT | CLOSE WINDOW |

| RT | FORMULA | COMPOUND NAME | MW |
| --- | --- | --- | --- |
| 21.760 | C:15,H:23,N:3,O:4, | ISOPROPALIN | 309.37 |
| 21.790 | C:14,H:16,Cl:1,N:5,O:5,S:1, | TRIASULFURON | 401.82 |
| 21.800 | C:10,H:5,Cl:7,O:1, | HEPTACHLOREPOXIDE-CIS | 389.32 |
| 21.810 | C:14,H:16,Cl:1,N:3,O:1, | METAZACHLOR | 277.75 |
| 21.840 | C:19,H:26,O:3, | ALLETHRIN | 302.41 |
| 21.900 | C:9,H:10,Br:1,Cl:1,N:2,O:2, | CHLORBROMURON | 293.55 |
| 21.900 | C:10,H:5,Cl:7,O:1, | HEPTACHLOREPOXIDE-TRANS | 389.32 |
| 21.930 | C:11,H:10,Cl:1,N:1,O:3,S:1, | BENAZOLIN-ETHYL | 271.72 |
| 21.960 | C:13,H:19,N:3,O:4, | PENDIMETHALIN | 281.31 |
| 21.990 | C:12,H:14,N:4,O:4,S:2, | THIOPHANATE-METHYL | 342.39 |
| 22.060 | C:13,H:15,Cl:2,N:3, | PENCONAZOLE | 284.19 |
| 22.060 | C:14,H:18,N:4,O:4,S:2, | THIOPHANATE-ETHYL | 370.44 |
| 22.080 | C:11,H:21,N:5,S:1, | DIMETHAMETRYN | 255.38 |
| 22.100 | C:12,H:27,P:1,S:3, | MERPHOS I | 298.50 |
| 22.110 | C:9,H:5,Cl:3,N:4, | ANILAZINE | 275.52 |
| 22.150 | C:14,H:12,Cl:2,O:1, | CHLORFENETHOL | 267.15 |
| 22.180 | C:11,H:13,F:3,N:2,O:3,S:1, | MEFLUIDIDE | 310.29 |
| 22.180 | C:10,H:13,Cl:2,F:1,N:2,O:2,S:2, | TOLYFLUANID | 347.25 |
| 22.230 | C:9,H:8,Cl:3,N:1,O:2,S:1, | CAPTAN | 300.59 |
| 22.360 | C:13,H:11,Cl:2,N:1,O:5, | CHLOZOLINATE | 332.14 |

FIG. 8

DIALOGUE BOX FOR AED PESTICIDE DATABASE SEARCH

SEARCH PESTICIDE DATABASE

FILTERING FOR SEARCH:

RET. TIME OF SEARCHED PEAK: 22.833 MINUTES
SEARCH TIME WINDOW 0.8 MINUTES
INCLUDE ELEMENTS: S  N  Cl  ☐ ☐ ☐ ☐
EXCLUDE ELEMENTS: P  F  Br  I  ☐ ☐ ☐ ☐

AED ELEMENT INFORMATION:

[SEARCH]    [CANCEL]

FIG. 9

SEARCH RESULTS USING ELEMENT DATA:
"INCLUDE" S,N,Cl
"EXCLUDE" P,F,Br,I

| | PESTICIDE SEARCH RESULTS | |
|---|---|---|
| START NEW REPORT | ADD RESULTS TO CURRENT REPORT | |
| VIEW CURRENT REPORT | CLOSE WINDOW | |

| RT | FORMULA | COMPOUND NAME | MW |
|---|---|---|---|
| 21.790 | C:14,H:16,Cl:1,N:5,O:5,S:1, | TRIASULFURON | 401.82 |
| 21.930 | C:11,H:10,Cl:1,N:1,O:3,S:1, | BENAZOLIN-ETHYL | 271.72 |
| 22.230 | C:9,H:8,Cl:3,N:1,O:2,S:1, | CAPTAN | 300.59 |

FIG.10

METHOD FOR SAMPLE IDENTIFICATION USING A LOCKED RETENTION TIME DATABASE

FIELD OF THE INVENTION

The present invention relates to methods for identification of unknown analytes of interest and, more particularly, creating a retention time database of analytes and their respective retention times under locked conditions such that analyses of interest separated by a GC system locked to the retention time database may be identified by reference to the retention time database.

BACKGROUND OF THE INVENTION

Gas chromatography is based on the premise that the combination of analytes making up a sample introduced into a column within a gas chromatograph separate as they transverse the column at different rates and subsequently exit the column at different retention times. Both operational parameters Column head pressure, carrier gas type and oven temperature) and column parameters (length, inside diameter, stationary phase type and thickness) contribute to an analyte's retention time.

In order to identify analytes of interest, chromatographers typically generate calibration tables for their GC systems based on sample chromatograms provided by column manufacturers. Calibration tables are generally specific to those analytes corresponding to a specific analysis and are only useful with the GC system on which they were created. It is known to generate a retention time calibration table by injecting a series of "standards" (corresponding to analytes of interest) into a reference gas chromatograph (GC) and measuring the retention time of the analytes in the GC. The reference GC includes a known column having a defined set of column parameters, and the GC is operated in accordance with a set of known operating parameters. Calibration table generation is very time consuming as hundreds of "standards" must be injected into the reference GC system employed for building the calibration table. For example, a pesticide calibration table might include some or all of the more than 700 pesticides currently registered for use in the world. A retention time calibration table may be helpful in identifying a pesticide separated in other GC systems having the same column and operating parameters as those used to form a pesticide retention time calibration table.

Unfortunately, variations between the column and operating parameters of the GC system used to form the calibration table, and those of another GC system may result in large variations in retention time. In particular, variations may be due to instrument calibration, atmospheric temperature and pressure changes, oven design, column length and column degradation. These variations may be compounded over time as it typically takes from weeks to years to conduct all of the analysis required to complete a detailed retention time calibration table. Even though it is difficult to replicate exact retention times set forth in a retention time calibration table, such a calibration table is useful in illustrating the relative relationship between retention times such that through trial and,error or lengthy cross-correlation, it is possible to positively identify unknown analytes of interest.

A popular "relative retention" approach to, using chromatographic databases utilizes retention indices or Kovats indices that circumvent problems in getting the same retention time from instrument-to-instrument, column-to-column. In general, all prior art chromatography calibration table protocols that have been successfully employed for identifying unknown analytes are based on either relative retention times (retention indexes) or retention times related to a specific GC system having specified column and operating parameters that do not change (for example, during column maintenance). Attempts to replicate the identical column and operating parameters on another GC system or after column maintenance, is virtually impossible.

It would be advantageous to develop a retention time database of analytes and their corresponding retention times through a column having known column parameters and operated on a reference GC system with known operating parameters that are not subject to the effect of calibration and atmospheric variations and that provides for system-to-system, time-to-time, location-to-location matching of retention times on other GC systems. Such a database could provide for identification of unknown analytes through the matching of retention times in the retention time database if another GC system having the same column and operational parameters could be locked to the reference GC system. There is a need for a method that can be used to compensate for differences in GC oven temperature calibration such that retention times can be reproduced accurately between different GC instruments even if they do not have the same actual GC oven temperature when set to the same nominal temperature. Normally, GC's having ovens that are not calibrated exactly the same will give chromatograms with different retention times for a given compound, even when running identical methods on identical GC columns.

There exists a need for narrow retention time windows in order to reduce the number of possible retention time matches and thus enhance differentiation between closely-eluting peaks. There exists a need for operating a GC system such that retention times of analytes passing through a known column on the GC system can be compared with the retention times of the same analytes passing through a different column having the same nominal column parameters in the same or even in a different gas chromatograph.

SUMMARY OF THE INVENTION

The invention provides a method for developing a retention time database of identified analytes and their respective retention times under locked conditions for identification of unknown analytes of interest eluting from any GC system locked to the same retention time database. The invention may also be employed in combination with selective detection for enhanced certainty of identification. The invention may also be employed with method translation to lock a GC system having operating and column parameters that are different than those used to form a retention time database when used in, combination with selective detection for enhanced certainty of identification. The invention may also be employed with method translation to lock a GC system having operating and column parameters that are different than those used to form a retention time database.

The retention time database is created under locked conditions by adjusting the column head pressure of a reference GC system such that the column void time or the retention time of a known analyte equals a defined value. A series of standards are injected into the reference GC system to form the reference database. To ensure that the reference GC system remains locked during development of the retention time database, the column head pressure is periodically adjusted such that the void time or retention time of the known analyte remains at the defined value.

A GC system may be locked to a retention time database by adjusting the column head pressure such that the column void time of the GC system matches the column void time of the column used to form the retention time database. The new head pressure compensates for differences in column dimensions and provides for retention time locking such that analytes exiting the new column can be identified by referencing the retention time- database. An adjustment to column head pressure may be ascertained by injecting into the GC system a known analyte or standard one or more times with the head pressure above the nominal pressure and one or more times below the nominal head pressure and graphing the retention time-vs-pressure relationships. In particular, the retention times-vs-pressure relationships may be graphed or mathematically curve fitted and for determining the adjustment to the current column head pressure to effect a lock.

Once a retention time database has been established, retention times of analytes passing through another GC system that is locked to the retention time database may be identified. A locked GC system typically employs the same nominal column and operating parameters as employed by the reference GC system. Alternatively, method translation may be employed to first translate database retention times to correspond to the column and operating parameters employed on a new GC with different column dimensions, phase ratio, or carrier gas type or flowrate. The new GC system parameters are also translated and locked such that the retention times of analytes of interest eluting from the new locked GC system are identical to those in the adjusted retention time database and can be accurately searched against the database for identification.

Analyte selective detectors may be employed in combination with a locked GC system to increase the possibility of positively identifying a particular analyte.

It would be advantageous to accurately translate retention times in a locked database generated using one carrier gas type and flow rate to a new database using another carrier gas type and flow rate, or to a new column of different phase ratio or dimensions.

It would be advantageous to provide for direct comparison of measured retention times from different chromatographic systems to a library of reference retention times obtained under very specific operating parameters and column parameters.

Further, such a retention time database could be advantageous when implemented by use of scaling factors corresponding to the retention time of a particular analyte divided by the void time (or proportional substitute) of the column, especially if the retention time database provides an improvement in any of the following areas: porting chromatographic methods to columns having different dimensions, phase ratios or different carrier gas types, converting retention times to and from retention index libraries/databases, or enhancing the synergy of GC systems by comparing different detector outputs for multiple analyses of the same sample.

Completely automated analyses may be obtained from the use of this method, including the use of a centralized database that is accessible from networks such as Internet enabled distributed chromatographs or data systems operating under locked conditions.

Other aspects and advantages of the present invention will be come apparent from the following detailed description, taken in conjunction with the accompanying drawings, illustrating by way of example the principles of the invention.

BRIEF DESCRIPTION OF THE DRAWINGS

FIG. 3 illustrates a formula employed for calculating a head pressure adjustment.

FIG. 4 is a screen display illustrating a retention time locking calculator.

FIG. 5 is a flowchart illustrating the invention employed in the analysis of pesticides in foods.

FIG. 8 is a screen display of a database search using a 0.8 min window (20 possibilities were reported).

FIG. 9 is a screen display of a database search which includes elemental information.

FIG. 10 illustrates the results of the search request of FIG. 9.

DETAILED DESCRIPTION OF THE PREFERRED EMBODIMENTS

The invention provides a method for generating a retention time database under locked conditions that is not subject to variations in column and operating parameters. Unknown analytes of interest eluting from a GC system locked to the retention time database have an increased probability of being identified by direct comparison of retention times. In particular, locked retention times provide for very narrow peak windows and narrow peak windows provides for differentiation between closely-eluting peaks. The invention provides for retention time locking within five to ten standard deviations of instrument accuracy.

Figure 1:
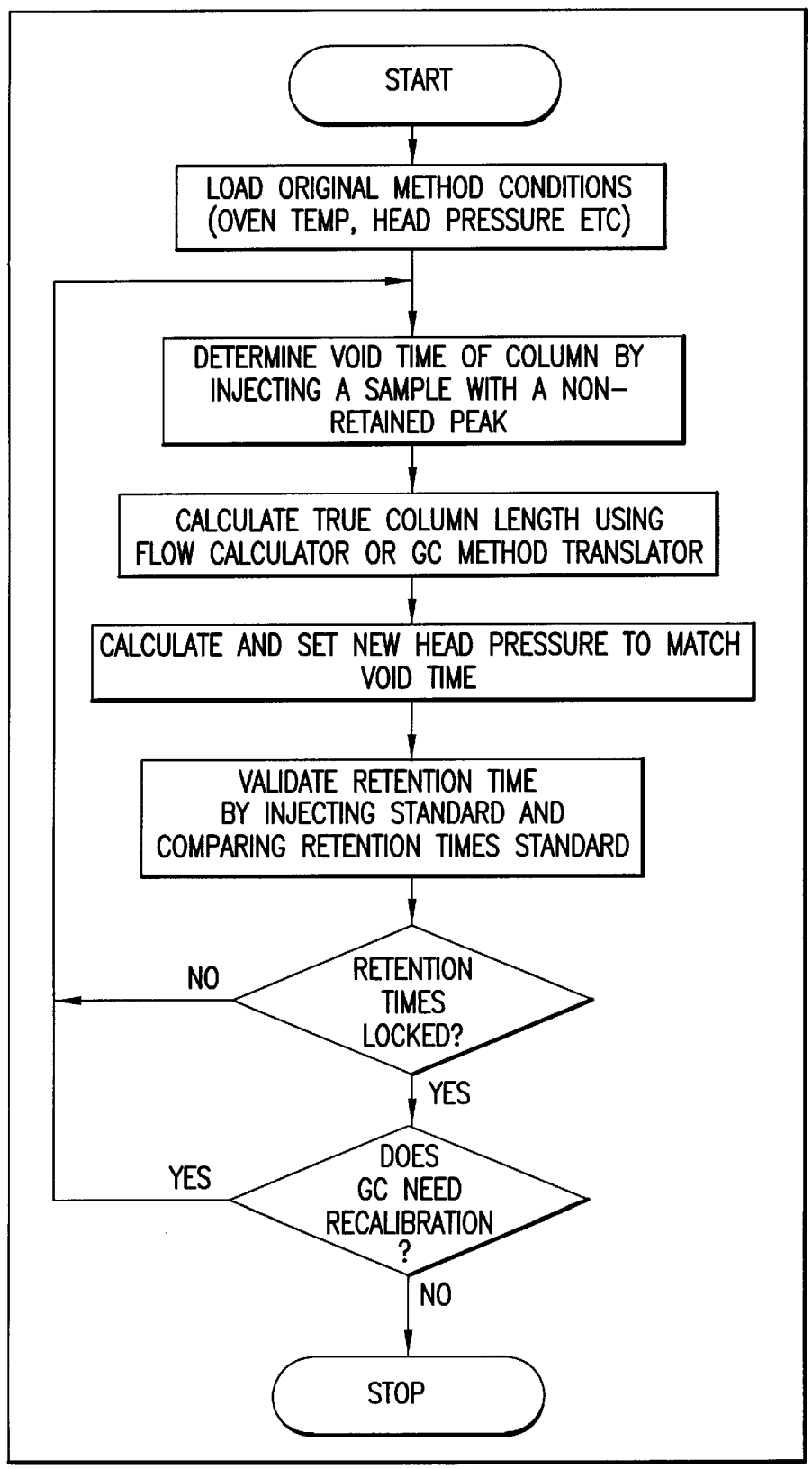
FIG. 1 is a flowchart highlighting method steps for retention time locking through matching of column void times.
Figure 2:
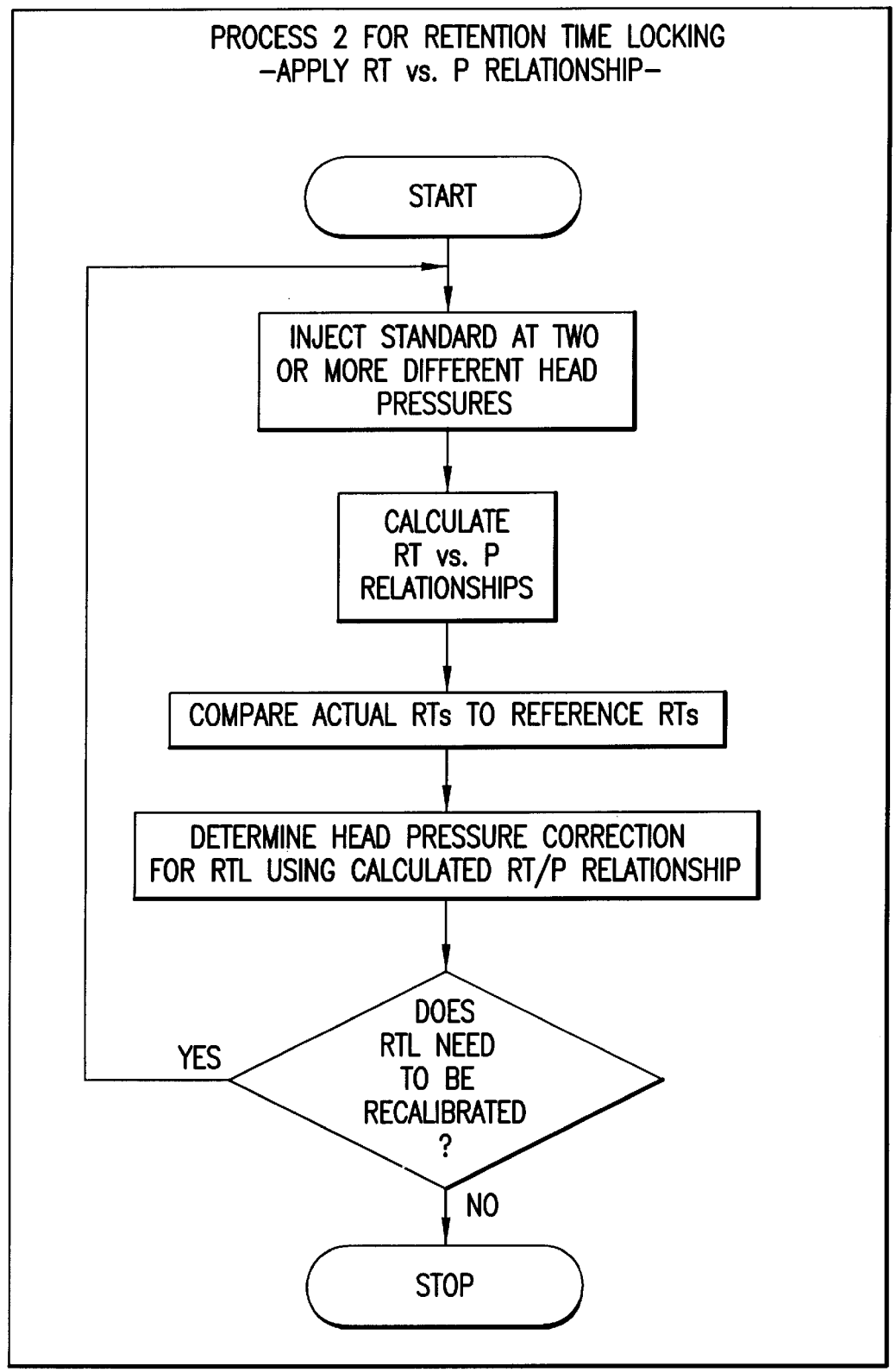
FIG. 2 is a flowchart highlighting the method steps for retention time locking based retention time versus pressure relationships.

Several methods for calculating an adjustment to the column head pressure required to lock a GC system are fully disclosed in commonly assigned U.S. patent application Ser. No. 08/728,868, filed on Oct. 10, 1996 entitled "Automated Retention Time Locking" and hereby incorporated by reference. In particular, the column head pressure of the locking GC system may be adjusted such that the column void time is matched to the column void time of the column employed for generating the retention time database. FIG. 1 is a flowchart highlighting method steps for retention time locking through matching of column void times. Using an alternative method as illustrated in FIG. 2, a known analyte or "standard" having a known or "reference" retention time is injected one or more times into a GC system having a column head pressure above a nominal pressure, and one or more times at a column head pressure below a nominal pressure. The actual measured retention times are compared to the reference retention times. Retention time versus the actual pressures employed are used for calculating an adjustment to the column head pressure that locks the GC system. Finally, the standard is injected again to validate that the GC system is locked. FIG. 3 illustrates a formula employed for calculating a head pressure adjustment where a GC system to be locked employs column and operating parameters that are not different than those employed for generating the retention time database.

Notwithstanding the ability to compensate for variations in column and operational parameters, retention time locking requires precise oven temperature control, identification of column parameters (dimensions, stationary phase chemistry and film thickness) and precise column-head pressure control. Precision of oven temperature control directly impacts precision of retention times. An example of an excellent oven design is exemplified in U.S. Pat. No. 4,181,613 on Jan. 1, 1980 to Welsh et. al. and hereby incorporated by reference. While temperature variations of only 0.1 degree centigrade result in retention time variations, retention time locking will accurately compensate for temperature variations of at least 5 degrees centigrade and still maintain a retention time lock of within 0.1 minute 6 second. While increasingly greater temperature variations can also be compensated for, the retention time lock will tend to vary by amounts greater than 0.1 degree which leads to increased retention time windows. Identification of column parameters are obtained by proper column selection prior to installation within the locking GC system and, through various known calibration procedures. For example, the Hewlett-Packard Company HP6890 GC has a "column calibration" function that based on some user inputs, can calculate the inside diameter of the column and the column length. Precise column head pressure control may be provided by electronic pressure control as set forth in U.S. Pat. No. 4,994,096 issued on Feb. 19, 1991 to Klein et. al. and commonly assigned to Hewlett-Packard Company which is hereby incorporated by reference. FIG. 4 is a screen display illustrating a retention time locking calculator. A software program (HP ChemStation) runs on a computer (not shown) and receives data from the GC system regarding the column head pressure and retention time for a standard injected five separate times (runs 1 through 5): Based on the actual pressures employed, the actual retention times, the retention time of a target peak and the current inlet or "column head pressure" and the formula previously set forth in FIG. 3, the calculator calculates a suggest pressure that will lock the retention times of the GC system. An automated self-locking system based on the retention time locking calculator advantageously provides for ease of use.

Method translation may also be employed for converting the retention times in the retention time database to correspond to a locked GC system having different column and operating parameters than those employed for generating the retention time database such that analytes of interest can be accurately searched in the retention time database by retention time. Implementation of method translation is disclosed in commonly assigned U.S. Pat. No. 5,405,432, issued on Apr. 11, 1995 to Snyder et al. and hereby incorporated by reference.

A retention time database created under locked conditions provides for enhanced certainty of identification. Unfortunately, separations in accordance with some analytical methods result in large numbers of analytes having retention times falling within even a relatively small retention time window. The combination of a locking GC system and an analyte selective detector will greatly increase the probability of identifying such analytes. Analyte selective detectors include, but are not limited to atomic emission (AED), electron capture (ECD), photo ionization (PID) or Mass Spectroscopy (MSD). The ability to create and search databases based on the actual retention times of analytes as opposed to relative retention times is a very valuable benefit of operating a locked GC system.

FIG. 5 is a flowchart illustrating the invention employed in the analysis of pesticides in foods. The retention time database is created under locked conditions as previously set forth. Pesticides are identified by locking a GC system to the pesticide retention time database by adjusting the column head pressure by void time matching, retention time matching or both as previously described. In particular, a preliminary identification of analytes eluting from the column can be made by comparing (manually or automatically) the measured retention time to those in the retention time database. The preliminary identification may be sufficient for some pesticide identification, however, if a number of potential pesticides have a relatively close retention time, additional discrimination is required.

Figure 6:
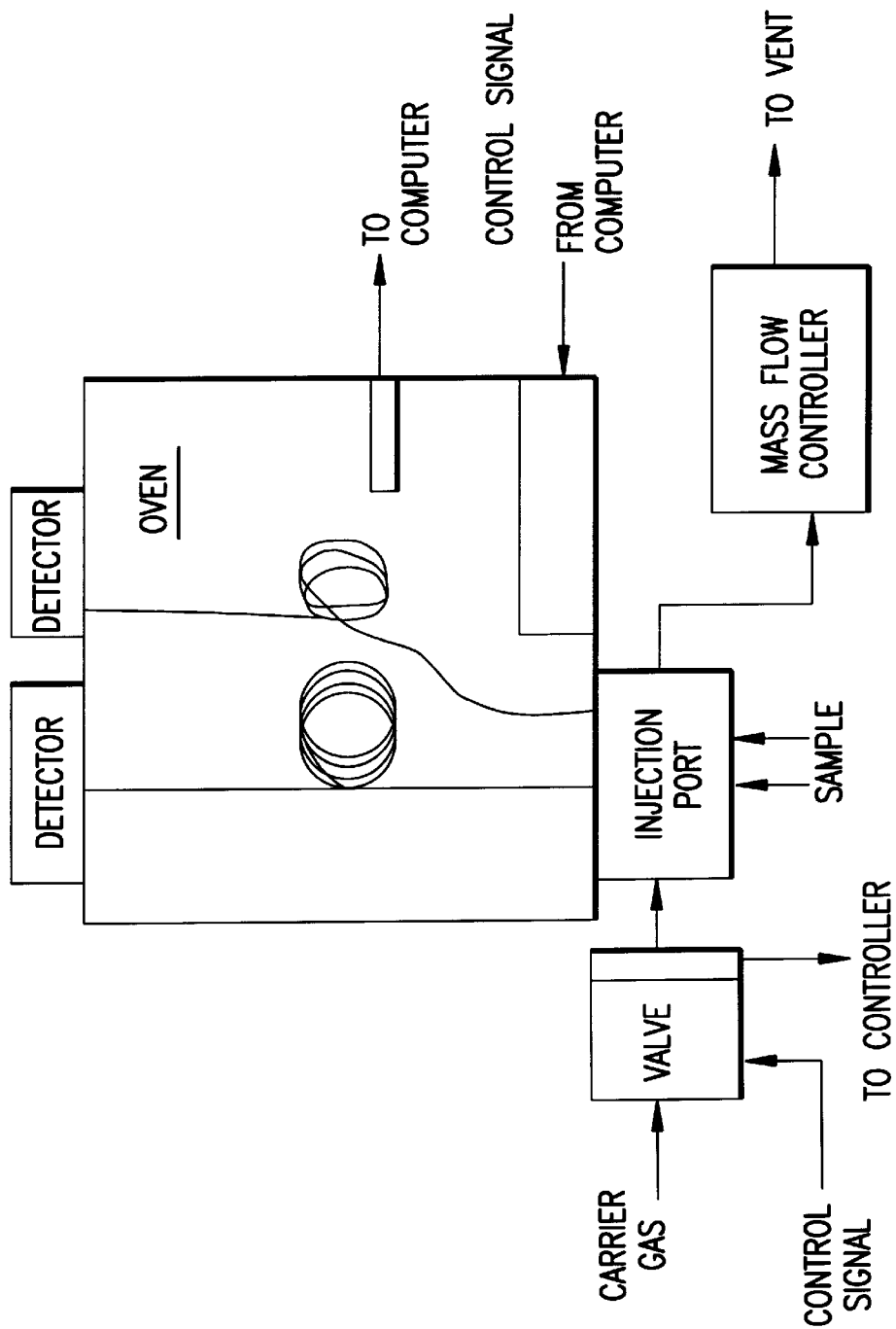
FIG. 6 illustrates a locking GC system having two columns operating in parallel.

FIG. 6 illustrates a locking GC system having two columns operating in parallel. The first column has a detector that is not necessarily an analyte selective detector, and a second column employs an analyte selective detector. The retention time corresponding to the preliminary identification is employed for ascertaining when analytes eluting from the column are directed to the selective detector. In the preferred embodiment, AED, ECD, PID, NPD (nitrogen phosphor detector) FIR (flame ionization detector) or MSD are employed as the analyte selective detectors for a second column running at the same conditions.

II. Detailed Example Illustrating the Identification of Pesticides

Advantages associated with the invention are evidenced in the following in which pesticides in fruit and vegetable extracts obtained from the Florida Department of Agriculture and Consumer Services (Tallahassee) and from the Canadian Pest Management Regulatory Agency, Laboratory Services Subdivision (Ottawa) were identified. A GC system having an analyte selective detector (AED) is locked to a pesticide database and a unique user interface is employed for identifying those pesticides most likely to be present and a GC/MS is employed for confirmation.

Table 1 lists the instrumentation as well as column and operating parameters used for GC/AED screening and GC/MS confirmation. Table 1. Instrumentation, operating and column parameters.

TABLE 1

Instrumentation, operating and column parameters.

| GC/AED System | |
|---|---|
| Gas chromatograph | HP 6890 |
| Automatic sampler | HP 6890 Series Automatic Sampler |
| Atomic Emission detector | HP G2350A Atomic Emission Detector |
| Computer for data acquisition & analysis | HP Vectra XM Series 4 5/150 |
| Software | HP G2360AA GC/AED Software running on MS Windows 3.11 |
| Column | 30 m × 0.25 mm × 0.25 µm HP-5MS |
| GC Inlet | Split/splitless, 250° C. or 280° C. |
| Injection volumes | 2 µL splitless or 5 µL pulsed splitless |
| Inlet pressure (splitless)[a] | 27.6 psi, constant pressure for 2-µL injections |
| Inlet pressure program (pulsed splitless)[a] | 60 psi (2.01 min), 10 psi/min to 27.9 psi (hold) |
| Oven temperature program | 50° C. (1.13 min), 30° C./min to 150° C. (2 min), 3° C./min to 205° C. (0 min), 10° C./min to 250° C. (20 min) |
| AED transfer line temperature | 260° C. |
| AED cavity temperature | 260° C. |
| AED elements & wavelengths (nm) | Group 1: C 496, Cl 479, Br 478<br>Group 2: C 193, S 181, N 174<br>Group 3: P 178 |
| GC/MS System | |
| Gas chromatograph | HP 6890 |
| Automatic sampler | HP 6890 Series Automatic Sampler |
| Mass spectral detector | HP 5973 MSD |
| Computer for data acquisition & analysis | HP Vectra XU 6/200 |

TABLE 1-continued

Instrumentation, operating and column parameters.

| | |
|---|---|
| Software | HP G1701AA Version A.03.00 running on MS Windows 95 30 m × 0.25 mm × 0.25 μm HP-5MS |
| Inlet | Split/splitless, 250° C. |
| Injection volume | 2 μL |
| Inlet pressure[a] | 14 psi (constant pressure) |
| Oven temperature program | Same as GC/AED |
| MSD Parameters | |
| Acquisition mode | Scan (35–550 amu) |
| Temperatures | Transfer line = 280° C., MS quad = 150° C., MS source = 230° C. |

[a]The column head pressures shown are typical values. Exact values were determined as part of the retention time locking procedure.

a) The column head pressures shown are typical values. Exact values were determined as part of the retention time locking procedure.

Retention Time Locking

Retention time locking is employed for matching analyte retention times from run to run, independent of the GC system, detector, or manufacturing variations in column dimensions; without method translation, the only requirement is that the columns used have the same stationary phase and the same nominal diameter and phase ratio. For example, with retention time locking, it is possible to match analyte retention times on a GC/AED (for example, as illustrated in FIG. 6) and a GC/MS even though the column outlet pressures are much different: 1.5 psi above ambient pressure for the AED and vacuum for the MSD. The procedure also compensates for differences in GC column length resulting from variations in manufacturing or from column cutting required during routine maintenance.

As previously set forth, retention time locking is accomplished by adjusting the GC column head pressure until a given analyte, such as an internal standard, has the required retention time. Once the GC system is locked, all other analytes in the chromatogram will have the correct retention times as well. Retention time locking provides for the building of a retention time database of measured pesticide retention times using a reference GC system and then reproduce those retention times in subsequent runs on the same or different GC systems. With this increased retention time precision and predictability, raw retention times become a far more useful indicator of analyte identity. For many years relative retention times or retention indices have been used to identify compounds; these techniques were developed to compensate for the fact that retention times were not generally predictable from day to day, column to column, or instrument to instrument. With modern instrumentation and retention time locking, raw retention times can be used for compound identification in much the same way that retention indices have been used in the past, albeit with much less effort. The chromatographer could simply scan a table of pesticide retention times, eliminating all possibilities but those with close elution times under the same locked GC conditions.

However, pesticides almost always contain heteroatoms and often have several in a single molecule; the most frequently encountered heteroatoms are O, P, S. N, Cl, Br, and F. GC/AED has been shown to be a useful tool for pesticide screening because it is selective for all of the elements found in these compounds However, any analyte selective detector is useful in narrowing down a compounds identity. Thus, GC/AED screening provides valuable information about the elemental content of an unknown molecule. By including this elemental information along with the retention time, it should be possible to narrow pesticide "hits" to just a few possibilities.

Pesticide Retention Time Table

A table of pesticide retention times and molecular formulas initially developed by Stan and Linkerhagner using a 25 m×0.32 mm ×0.17 μm HP-5 column and an atomic emmission detector, is translated to a a 30 m×0.25 mm×0.25 μm HP-5MS column. Further adjustments to the 408 retention times were made by curve fitting the actual retention times for 60 known compounds and applying the corrections to the table.

Pesticide Screening Method

Figure 7:
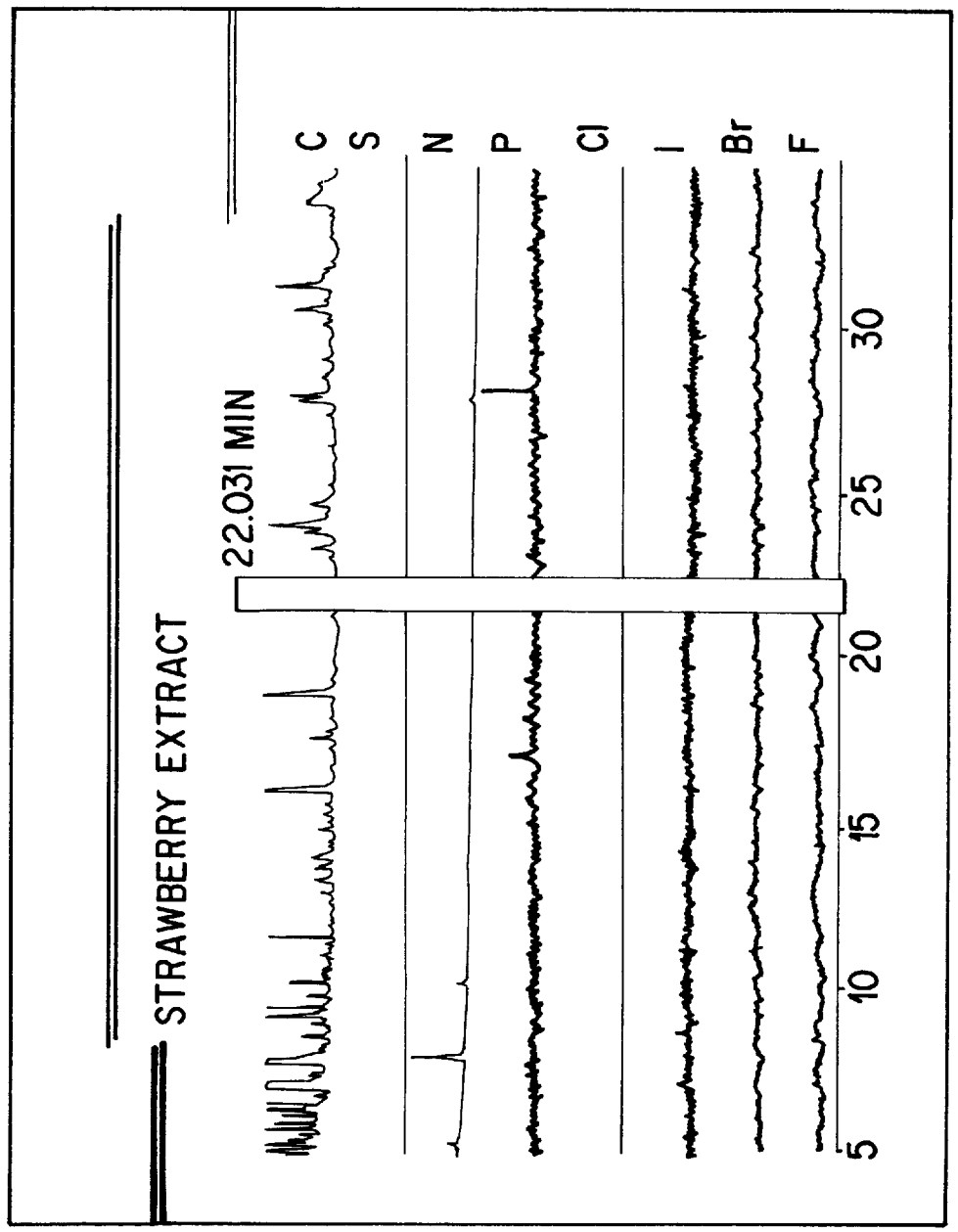
FIG. 7 shows a set of GC/AED element-selective chromatograms obtained for a strawberry extract.

First, retention time locking was used to match GC/AED and GC/MS analyte retention times to those listed in the translated pesticide database. FIG. 7 shows a set of GC/AED element- selective chromatograms obtained for a strawberry extract. Peaks in the S, N, P, and Cl chromatograms suggest the presence of several pesticides. The peak at 22.031 min contains S, N, and Cl but does not appear to have any P, F, Br, or I. FIG. 8 illustrates the results of searching the database only on the basis of the peak's retention time using a 0.8 min window (20 possibilities were reported). However, including elemental information in the search (FIG. 9), reduces the number of possibilities to only three of the 408 pesticides in the database (FIG. 10).

This example highlights the advantages of using retention time locking to obtain a preliminary identification of possible analytes of interest and a narrowing the window of possible retention times, followed by selective detection with retention time locking to increase selectivity.

A search time window is chosen that is wide enough to be sure to include the correct analyte, but narrow enough to eliminate as many extraneous "hits" as possible. A value of 0.8 min was chosen because tests with several dozen compounds showed that, under locked conditions, pesticide retention times always fell within ±0.3 min of the tabulated value. This time window would be smaller if one were to use a database generated on the same column under locked conditions. Of course, a narrower time window would generate fewer hits and a more accurate screening method.

From the GC/AED chromatograms it is usually possible to determine which heteroatoms are present or absent in the suspected pesticide peak. All available information is added to the dialog box and this is used to focus the search on those pesticides that fall within the retention time window and have the specified elemental content.

Confirmation is usually done by GC/MS under locked conditions so that all GC/MS retention times match the GC/AED values. Alternatively, when there is adequate signal to quantitate the analyte in multiple AED element-selective chromatograms, it is often possible to confirm a pesticide's identity simply by calculating its heteroatom ratio. GC/AED software for element ratioing facilitates this procedure. A second column with a different phase may be employed for confirmation, however a new retention time database on the confirmation column must be developed.

Retention time locking allows chromatographers to match retention times with far more accuracy than was routinely possible in the past. By creating a database from the beginning on the preferred GC column under locked conditions, it is possible to narrow the required search window and results in fewer hits and greater accuracy.

While GC/AED is an ideal tool for element-selective pesticide screening, many laboratories rely on a combination of other selective detectors. It should still be possible to apply this method if each GC system runs the same method under the same locked conditions. Whatever elemental data that is available could be entered into the search dialog box. It may often be possible to identify a pesticide by using two different GC columns each configured with the same type of element-selective detector. For example, a pair of flame photometric detectors could be used to isolate organophosphorus pesticides on two different GC columns. Two databases could be searched and only those compounds that appear in both lists would be possibilities. Retention time locking with database searching could easily be applied to similar types of analyses. For example, one might use the procedure to identify polychlorinated biphenyls, polynuclear aromatics, or flavor and fragrance compounds.

While the invention has been described and illustrated with reference to specific embodiments employing retention time locking in combination with method translation, AED and GC/MS for pesticide identification, those skilled in the art will recognize that the invention works equally well in the identification of other analytes of interest typically identified through known GC techniques. Those skilled in the art will also recognize that depending on the type of column and operating parameters employed in the locked GC system, method translation may not be required. Additionally, there exists many analyte specific detectors other than AED and GC/MS that can be employed in combination with the invention to assist in identifying unknown analytes having retention times ascertained under locked conditions.

What is claimed is:

1. A method for developing a retention time database of identified analytes and their retention times on a reference GC system operated under locked conditions and the identification of unknown analytes of interest eluting from a locking GC system locked to the retention time database where each of said reference GC system and said locking GC system has a GC column operated at a column head pressure, comprising the method steps of:

adjusting the column head pressure of the reference GC system such that the column void time or the retention time of a known analyte is maintained at a defined value, injecting a series of known analytes into the reference GC system and recording the corresponding retention times, wherein a retention time database is generated, adjusting the column head pressure on the locking GC system such that the column void time of the column in the locking GC system is matched with the column void time in the reference GC system, or by adjusting the column head pressure on the locking GC system such that the retention time of a known analyte is matched to the corresponding retention time in the retention time database, wherein, the new head pressure compensates for differences in column dimensions, phase ratio, GC oven calibration, and provides for retention time locking such that analytes exiting the column in the locking GC system can be identified by referencing the retention time database.

2. The method for developing a retention time database and the identification of unknown analytes as claimed in claim 1, the step of adjusting the column head pressure further comprising the step of obtaining a series of retention time/pressure relationships of a sample by making one or more injections with the head pressure above the nominal pressure and one or more injections with the head pressure below the nominal head pressure, graphing the retention time/pressure relationships to determine the adjustment to the current head pressure to effect a lock.

3. The method for developing a retention time database and the identification of unknown analytes as claimed in claim 1, further comprising the step of ensuring that the retention time GC system remains locked during development of the reference database by periodically checking the void time or the retention time of a known analyte and adjusting the column head pressure to ensure that the void time or the retention time remains at a defined value.

4. The method for developing a retention time database and the identification of unknown analytes as claimed in claim 1, further comprising the step of translating the retention time database such that the retention times correspond to a locking GC system having different column and/or operating parameters as employed by the reference GC system.

5. The method for developing a retention time database and the identification of unknown analytes as claimed in claim 1, further comprising the step of translating the column and operating parameters of the locking GC system to correspond to the column and operating parameters employed for generating the retention time database, locking the locking GC system to the retention time database such that the retention times of analytes of interest eluting from the locked GC system may be matched to the retention times stored in the retention time database.

6. The method for developing a retention time database and the identification of unknown analytes as claimed in claim 1, further comprising the step of employing an analyte selective detector on the locking GC system to provide enhanced certainty of identification of an analyte of interest that elutes at a predetermined retention time as set forth in the retention time database.

7. The method for developing a retention time database and the identification of unknown analytes as claimed in claim 1, the method of locking the locking GC system further comprising the steps of:

injecting a non-retained compound into the locking GC system and operating the locking GC system in accordance with the prescribed operating parameters, measuring the time it takes a non-retained peak to exit the column (void time), calculating a new column head pressure, wherein the new column head pressure compensates for differences in column and operating parameters such that the GC system is now locked and analytes of interest may be identified by direct comparison of the measured retention times to retention times in the retention time database.

8. The method for using a retention time database comprising identified analytes and their respective retention times as claimed in claim 7, the method step of calculating a new column head pressure further using run time/pressure relationships to more precisely identify retention time in which a sample is injected with the head pressure above the nominal pressure, and a sample is injected with the head pressure below the nominal head pressure, wherein the retention times ascertained with these injections are graphed and employed for determining the adjustment to the current head pressure to effect a lock.

* * * * *